US012612351B2

(12) United States Patent (10) Patent No.: US 12,612,351 B2
Bennett et al. (45) Date of Patent: Apr. 28, 2026

(54) PROCESS FOR HYDROFORMYLATION WITH REMOVAL OF DISSOLVED HYDROGEN

(71) Applicant: JOHNSON MATTHEY DAVY TECHNOLOGIES LIMITED, London (GB)

(72) Inventors: Iryna Bennett, London (GB); Michael Gavin John Williams, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 613 days.

(21) Appl. No.: 18/003,995

(22) PCT Filed: Aug. 17, 2021

(86) PCT No.: PCT/GB2021/052131
§ 371 (c)(1),
(2) Date: Dec. 30, 2022

(87) PCT Pub. No.: WO2022/038350
PCT Pub. Date: Feb. 24, 2022

(65) Prior Publication Data
US 2024/0043363 A1 Feb. 8, 2024

(30) Foreign Application Priority Data
Aug. 19, 2020 (GB) ..................................... 2012930

(51) Int. Cl.
| | |
|---|---|
| *C07C 45/50* | (2006.01) |
| *B01J 31/18* | (2006.01) |
| *B01J 31/24* | (2006.01) |
| *C07C 45/78* | (2006.01) |
| *C10K 1/00* | (2006.01) |

(52) U.S. Cl.
CPC ........... *C07C 45/505* (2013.01); *B01J 31/185* (2013.01); *B01J 31/2404* (2013.01); *C07C 45/783* (2013.01); *C10K 1/002* (2013.01); *B01J 2231/321* (2013.01); *B01J 2531/004* (2013.01); *B01J 2531/822* (2013.01); *C07C 2531/02* (2013.01)

(58) Field of Classification Search
CPC .... C07C 45/505; C07C 45/783; B01J 31/185; B01J 31/2404
See application file for complete search history.

(56) References Cited

U.S. PATENT DOCUMENTS

| | | | |
|---|---|---|---|
| 4,148,830 A | 4/1979 | Pruett et al. | |
| 4,577,043 A | 3/1986 | Kalbfell et al. | |
| 4,950,462 A | 8/1990 | Nakao et al. | |
| 5,087,763 A | 2/1992 | Sorensen | |
| 5,382,417 A | 1/1995 | Haase | |
| 5,773,665 A | 6/1998 | Silverman et al. | |
| 6,500,991 B2 | 12/2002 | Wiese et al. | |
| 6,914,162 B2 * | 7/2005 | Richter .................. | C07C 45/50 |
| | | | 568/454 |
| 2004/0024259 A1 | 2/2004 | Richter et al. | |
| 2019/0023637 A1 | 1/2019 | Simpson et al. | |

FOREIGN PATENT DOCUMENTS

| | | | |
|---|---|---|---|
| EP | 2297077 A1 | 3/2011 |
| JP | S60-112733 A | 6/1985 |
| JP | H08-92146 A | 4/1996 |
| JP | 2019-508450 A | 3/2019 |
| TW | 329396 B | 4/1998 |
| WO | 2016/089602 A | 6/2016 |

OTHER PUBLICATIONS

J.A. Hogendoorn, et al., "The absorption of carbon monoxide in COSORB solutions: absorption rate and capacity", W.P.M. van Swaaij, G.F. Versteeg, The Chem. Eng. Journ. 59 (1995) 243-252; accepted Nov. 5, 1994.

* cited by examiner

*Primary Examiner* — Sikarl A Witherspoon
(74) *Attorney, Agent, or Firm* — BakerHostetler

(57) ABSTRACT

A process for producing an aldehyde is disclosed. The process comprises: hydroformylating an olefin to form the aldehyde using a hydroformylation catalyst; recovering an effluent stream comprising the aldehyde, hydrogen and the hydroformylation catalyst; passing the effluent stream to a stripper; contacting the effluent stream with a strip gas in the stripper to produce a stripped effluent stream having a lower hydrogen concentration than the effluent stream; and recovering the stripped effluent stream.

12 Claims, 2 Drawing Sheets

PROCESS FOR HYDROFORMYLATION WITH REMOVAL OF DISSOLVED HYDROGEN

FIELD OF THE INVENTION

The present invention relates to a process for hydroformylation of an olefin to produce an aldehyde. In particular, but not exclusively, the present invention relates to a process for hydroformylation of a mixture of $C_8$ olefin isomers to produce a $C_9$ aldehyde. The present invention also relates to a process for hydroformylation of an olefin to produce an aldehyde, the process including removal of dissolved hydrogen from a reactor product prior to entering a separation unit.

BACKGROUND

The hydroformylation of olefins to produce aldehydes is performed industrially on a large scale. The aldehydes are typically intermediate products in the production of alcohols, acids or esters. A well-known process for producing such products is the LP Oxo process provided by Dow and Johnson Matthey Davy Technologies. In a typical flowsheet, for example as described in U.S. Pat. No. 4,148,830 or U.S. Pat. No. 5,087,763, hydroformylation is performed in the liquid phase using a ligand-rhodium catalyst. A liquid phase reactor effluent is taken from the hydroformylation reactor and fed to a catalyst separation unit where a liquid catalyst solution is separated from the product aldehyde. The liquid catalyst solution is then returned to the reactors. The liquid catalyst solution typically comprises a solvent, rhodium, a ligand, and other components present in the reactor.

Many variations of molecules that can function as a ligand are known. Commercially used ligands are often phosphines, such as triphenylphosphine; monophosphites, such as tri methylolpropanephosphite or tris(2,4-di-tert-butylphenyl)phosphite; bisphosphites; or mixtures of any of these. WO2016089602 lists various ligands. Of these 3 types of ligands, monophosphites are believed to be the most active but also to have the weakest ligand to rhodium interaction which is believed to result in a less stable catalyst complex.

A typical catalyst separation unit comprises a vaporiser in which part of the reactor effluent is vaporised. This results in a vapour phase containing the aldehyde product and essentially free of catalyst, and a liquid phase containing the liquid catalyst solution. The vapour phase is forwarded for further processing. The further processing generally includes an aldehyde purification stage, wherein unconverted olefins and paraffins are removed along with dissolved syngas and other light components. The aldehydes thus produced are typically used as intermediates for other products such as alcohols, acids or esters, which may typically be used as plasticisers.

The vaporising of the aldehyde in the reactor effluent in the catalyst separation unit is assisted by lower pressures and higher temperatures in the vaporiser. However, the liquid catalyst solution is normally sensitive to degradation of various forms resulting in loss of activity and loss of rhodium. Rhodium is a valuable precious metal and thus it is desirable for consumption of rhodium to be as low as possible in order to maintain an economical process. This often dictates the maximum allowable temperature in the vaporiser. Evaporation can still be increased by operating the vaporiser at a low pressure. Lower total pressure implies a low partial pressure of the aldehyde, which increases the evaporation of aldehyde and is particularly useful for relatively heavy aldehydes. However, a lower total pressure, and especially a vacuum, results in larger equipment volumes and thus more expensive equipment. At pressures lower than atmospheric pressure a risk also arises of air finding its way inside the process. That can result in the oxidation of the aldehyde and/or ligand, both of which result in increased costs.

It is thus desirable to stabilise the catalyst to prevent losses and desirably to permit the use of higher temperatures and above-atmospheric pressures.

U.S. Pat. No. 6,500,991 aims to stabilise the catalyst by cooling the catalyst solution obtained from the vaporiser and adding a carbon monoxide containing gas to the liquid, or by adding carbon monoxide to a flash vessel prior to the catalyst separation.

EP2297077 describes the use of a circulating strip gas in order to lower the partial pressure of the aldehyde but maintain an overall positive pressure. In the catalyst separation unit, the reactor effluent is fed to a vaporiser together with the strip gas, and both flow co-currently through the vaporiser. The strip gas is essentially free of aldehydes and thus reduces the aldehyde partial pressure in the vaporiser, thereby increasing the driving force for the aldehyde to evaporate from the reactor effluent. The vaporiser may also be heated to further stimulate evaporation. The resulting vapour mixture, comprising the aldehyde and the strip gas, is then separated from the remaining liquid catalyst solution. The liquid catalyst solution is returned to the reactor and the vapour mixture is fed to a condenser. In the condenser, the temperature of the vapour mixture is decreased with the result that essentially all the aldehyde is condensed and separated from the remaining vapour. The remaining vapour is then recompressed to the inlet pressure of the vaporiser and re-used as strip gas.

WO2016089602 describes the addition of carbon monoxide to the vaporiser strip gas in order to reduce catalyst losses. It also suggests that low hydrogen partial pressures in the strip gas can contribute to low catalyst losses. The carbon monoxide can be obtained by separating syngas into a hydrogen-containing stream and a make-up strip gas stream.

It has been found that hydrogen dissolved in the reactor effluent stream may evolve into the circulating strip gas and will accumulate if not purged out. As a result, a large flow of make-up gas such as carbon monoxide may be required to maintain the hydrogen concentration in the circulating strip gas at a sufficiently low level. There remains a need for a process that can address the issues surrounding hydrogen in the reactor effluent stream whilst minimizing the need for additional syngas feedstock and energy input and reduction in size of the equipment, which is required to produce the CO-rich stream for the strip gas and for the recovery of the purged CO-rich gas for useful purposes.

The present invention seeks to ameliorate some of the problems with the prior art. In particular, but not exclusively, the present invention seeks to provide an improved, more cost-effective process for the hydroformylation of olefins to aldehydes.

SUMMARY OF INVENTION

According to a first aspect of the invention, there is provided a process for producing an aldehyde, the process comprising:
  a. hydroformylating an olefin to form the aldehyde using a hydroformylation catalyst;
  b. recovering an effluent stream comprising the aldehyde, hydrogen and the hydroformylation catalyst;

c. passing the effluent stream to a stripper;
d. contacting the effluent stream with a strip gas in the stripper to produce a stripped effluent stream having a lower hydrogen concentration than the effluent stream; and
e. recovering the stripped effluent stream.

Thus, the invention involves a stripper, for removing hydrogen from the effluent stream prior to the effluent stream entering a catalyst separation unit. As used herein, a stripper may encompass any suitable unit for removing hydrogen from solution. In a catalyst separation unit, the catalyst is separated from the effluent stream, concentrated in a liquid phase, and preferably recycled to the hydroformylation reactor to once again participate in the reaction. The catalyst separation is generally performed at elevated temperatures and reduced pressures. At these conditions, it was found that the presence of hydrogen may be detrimental to catalyst stability. Further, the hydrogen dissolved in the reactor effluent stream may evolve into the circulating strip gas and will accumulate if not purged out. As a result, a large flow of make-up gas such as carbon monoxide is generally required to maintain the hydrogen concentration in the circulating strip gas at a sufficiently low level.

This invention provides for removing hydrogen dissolved from the reactor effluent stream upstream of the catalyst separation unit. By reducing the amount of hydrogen going to the strip gas as dissolved gases from the reactor effluent stream, this invention drastically reduces the purging required in the strip gas loop in order to maintain the low hydrogen concentrations which are necessary for catalyst stability. Because less purging is required, the process thereby requires less make-up gas such as carbon monoxide. As a direct result, the inventive process reduces equipment costs in the separation package and lowers the recompression requirements in order to return the purge to the hydroformylation reactors. Therefore, the invention provides significant benefits of maintaining catalyst activity, minimizing the need for additional feedstock, and allowing for smaller equipment. Further, the flow of gas required to maintain low partial pressure of hydrogen in the circulating strip gas is drastically reduced, thus this invention brings about a significant reduction in overall power consumption and equipment cost. The flow of CO-rich gas to the stripper in the proposed scheme is less than 1.5 mol % of the make-up gas required to achieve same content of hydrogen in cycle gas in the arrangement where CO-rich gas is sent directly to the loop as make-up gas.

Removal of hydrogen from the effluent stream may be accomplished by contacting the effluent stream with a strip gas. Contact between the effluent stream and the strip gas may be achieved in any suitable manner. Examples include but are not limited to: co- or counter-current flow of the strip gas and effluent stream through a column containing structured or random packing; or bubbling the strip gas through a flash vessel containing the effluent stream. In some aspects, the effluent stream may be flashed at a lower pressure in a flash vessel prior to introducing it to the stripper.

In some aspects, the strip gas comprises carbon monoxide, carbon dioxide, alkane, or combinations thereof. Preferably, the strip gas comprises carbon monoxide. The process may include feeding a syngas stream to a separation system, separating the syngas stream into a hydrogen rich stream and a carbon monoxide rich stream in the separation system, and using the carbon monoxide rich stream as the strip gas. Preferably, the carbon monoxide rich stream includes hydrogen in an amount of 0 mol % to 10 mol %;

less than 5 mol %; or less than 2 mol %. Preferably, the carbon monoxide rich stream includes carbon monoxide in an amount of 90 mol % to 100 mol %; greater than 95 mol %; or greater than 98 mol %. The separation system may include, for example, a membrane or a cryogenic distillation unit.

In some aspects, the process includes recovering a used strip gas stream, the used strip gas stream comprising the strip gas and hydrogen, from the stripper. The used strip gas stream may be combined with the hydrogen rich stream to form a recombined syngas stream, and the recombined syngas stream may then be fed to the hydroformylation reactor.

The process may include splitting the syngas stream fed to the separation system from a syngas feed stream to the hydroformylation reactor. In some aspects, the recombined syngas stream may be fed to the hydroformylation reactor by mixing the recombined syngas stream with the syngas feed stream.

Preferably, the hydrogen should be completely or substantially removed from the stripped effluent stream. In some aspects, the stripped effluent stream includes hydrogen in an amount of less than 0.5 mol %; less than 0.1 mol %; less than 0.05 mol %; or 0 mol % to 0.02 mol %; The process may further comprise feeding the stripped effluent stream to a vaporiser and recovering from the vaporiser a vapour stream comprising: (1) the aldehyde, and (2) a liquid catalyst recycle stream comprising the hydroformylation catalyst for recycle to the hydroformylation reactor. In some aspects, the concentration of hydrogen in the vaporiser is not more than 5 mol %; 3 mol %; or 1 mol %. The process may also include feeding a gas comprising carbon monoxide to the vaporiser.

The stripped effluent stream may proceed to a catalyst separation unit, for separating a catalyst such as a ligand-rhodium catalyst from the effluent of a hydroformylation reaction zone, wherein a circulating strip gas may be used in a vaporiser that separates the product aldehyde from the ligand-rhodium catalyst, wherein the circulating strip gas may be purged, for example to prevent build-up of hydrogen and inert components, with make-up carbon monoxide rich gas being added to the circulating strip gas, typically from a syngas separation unit. The purged strip gas, which is still rich in carbon monoxide, may be combined with a hydrogen-containing stream, typically also from the syngas separation unit, to form a re-formed syngas stream that is fed to the reaction zone.

The make-up strip gas stream may comprise carbon monoxide and is preferably rich in carbon monoxide. Preferably the make-up strip gas stream is from 50-100 mol % carbon monoxide, more preferably the make-up strip gas stream is from 70-100 mol % carbon monoxide, yet more preferably the make-up strip gas stream is from 80-100 mol % carbon monoxide, most preferably the make-up strip gas stream is from 97-100 mol % carbon monoxide. Higher concentrations of carbon monoxide are favoured as they allow for a higher concentration of carbon monoxide in the strip gas. Preferably the hydrogen-containing stream is from 50-100 mol % hydrogen, more preferably the hydrogen-containing stream is from 70-100 mol % hydrogen, yet more preferably the hydrogen-containing stream is from 80-100 mol % hydrogen, most preferably the hydrogen-containing stream is from 95-100 mol % hydrogen. In some embodiments the partial pressure of carbon monoxide in the vapour mixture leaving the vaporiser may be at least 15 psi (103 kPa) and preferably at least 20 psi (138 kPa). For example, the partial pressure of carbon monoxide in the vapour mixture leaving the vaporiser may be from at least 15 psi (103 kPa) to not more than 200 psi (1379 kPa). The partial pressure of hydrogen in the vapour mixture leaving the vaporiser may, for example, be not more than 10 psi (69 kPa); not more than 5 psi (34 kPa); or not more than 1 psi (6.9 kPa).

The process may comprise separating a syngas stream, where the syngas stream is split off from a main syngas feed and comprises carbon monoxide and hydrogen, into the hydrogen-containing stream and the make-up strip gas stream being fed to the stripping section and/or to the vaporiser. As described above, such syngas separation section may be located upstream of the hydrogen stripper. The syngas feed may be fed to the reaction zone after being recombined with the carbon monoxide and hydrogen from the strip gas in the vaporiser and the strip gas in the hydrogen stripper along with the hydrogen rich stream from the syngas separation section, to create a re-formed syngas stream. In some embodiments, for example, a syngas feed may arrive at the battery limit of the process and a portion of that syngas feed may be separated into the make-up strip gas stream and hydrogen-containing stream with the other portion of that syngas feed may be fed to the reaction zone. In such cases, some of the syngas feed effectively bypasses the catalyst separation unit. Such an arrangement may be beneficial in balancing the requirements for feeding syngas to the reaction zone and carbon monoxide to the strip gas. In such embodiments the molar ratio of the portion of the syngas feed separated into the make-up strip gas stream and the hydrogen-containing stream and the portion of the syngas feed fed to the reaction zone as the fresh syngas stream may preferably be from 0.01 to 1. More preferably the molar ratio is 0.05 to 0.5, and most preferably the molar ratio is 0.1 to 0.3. The molar ratio may be selected based on the separation efficiency, for example the membrane separation efficiency if a membrane is used for the separation. For example, if the make-up strip gas stream contains a relatively high level of hydrogen, a higher flowrate of make-up strip gas stream may be used.

The molar ratio of carbon monoxide fed to the reaction zone to olefin fed to the reaction zone is preferably about 1. The separating of the syngas stream into the hydrogen-containing stream and the make-up strip gas stream is preferably carried out using a membrane separation unit. Such membrane separation units are commercially available from companies such as MTR and Air Products. The membrane separation unit may be capable of achieving very high, such as at least 95 mol % or preferably at least 99 mol %, concentrations of carbon monoxide in the make-up strip gas stream in an economical way. Such high purities may however require a high flowrate of syngas to the membrane separation unit and it is therefore important that the carbon monoxide is not wasted. This is achieved in the present invention by the recombination of the purged strip gas stream with the hydrogen-rich stream to create the re-formed syngas stream that is passed to the reaction zone. Alternatively, or additionally, the separating of the syngas stream into the hydrogen-containing stream and the strip gas stream may be carried out using the COSORB process or variations of it, such as described, for example, in *The absorption of carbon monoxide in COSORB solutions: absorption rate and capacity* J. A. Hogendoorn, W. P. M. van Swaaij, G. F. Versteeg, The Chem. Eng. Journ. 59 (1995) 243-252 or in U.S. Pat. No. 4,950,462 or in U.S. Pat. No. 5,382,417. Alternatively, or additionally, the separating of the syngas stream into the hydrogen-containing stream and the strip gas stream may be carried out using low temperature absorption with liquid nitrogen.

The molar ratio of hydrogen to carbon monoxide in the syngas stream is preferably from 0.5 to 2.0. The most desirable ratio of hydrogen to carbon monoxide may depend on the desired hydrogen and carbon monoxide partial pressures in the reaction zone. Preferably the molar ratio of hydrogen to carbon monoxide in the re-formed syngas stream is similar to, for example within 10% of, the molar ratio of hydrogen to carbon monoxide in the syngas stream. It may be that the molar ratio of hydrogen to carbon monoxide in the re-formed syngas stream is preferably from 0.5 to 2.0. Hydrogen and carbon monoxide partial pressures in the reaction zone may influence the hydroformylation reaction, rate and selectivity. It may advantageously be simpler to control the partial pressures of carbon monoxide and hydrogen in the reaction zone if the molar ratio of hydrogen to carbon monoxide in the re-formed syngas stream is similar to the molar ratio of hydrogen to carbon monoxide in the syngas stream.

The vaporiser is preferably a falling film vaporiser, but may be other types of vaporiser including, for example, a vessel containing structured or random packing. The strip gas may be fed to the vaporiser in co-current or counter-current flow to the reactor effluent.

Since the recycle strip gas will be at a lower pressure than the strip gas due to pressure drops in the process, a compressor is preferably provided to compress the recycle strip gas before it is combined with the make-up strip gas. A compressor is also preferably provided to compress the re-formed syngas stream before it is fed to the reaction zone. Preferably the purged strip gas stream is purged from the recycle strip gas after the recycle strip gas is compressed. In that way, the purged strip gas stream may be at a suitable pressure for combining with the hydrogen-containing stream to form the re-formed syngas stream, which can then be compressed before feeding to the reaction zone, and separate compressors on the recycle strip gas and purged strip gas stream are avoided.

Typically, the reaction zone is operated at around 20 bar (2 MPa), for example from 15 to 40 bar (1.5 to 4.0 MPa), and the vaporiser is operated at around 8 bar (800 kPa), for example from 1 to 20 bar (100 to 2000 kPa). However, pressures of from 50 to 235 bar (5 to 23.5 MPa) are also known for operating the reaction zone.

Preferably the olefin is a $C_2$ to $C_{16}$ olefin, more preferably a $C_4$ to $C_{12}$ olefin and most preferably a $C_8$ olefin. The olefin is preferably a mono-olefin. The olefin is preferably an acyclic olefin, for example a linear olefin or a branched olefin. For example, the olefin may be propylene or normal butene. The olefin is preferably a $C_8$ olefin however, for example octene, dimerised butene or oligomerised ethylene. Preferably the aldehyde has one more carbon than the olefin. Thus, the aldehyde is preferably a $C_3$ to $C_{17}$ aldehyde, more preferably a $C_5$ to $C_{13}$ aldehyde and most preferably a $C_9$ aldehyde. The skilled person will understand that the aldehyde produced depends on the olefin used.

The invention can be used with any suitable ligand system that benefits from a carbon monoxide enriched strip gas. Preferably the ligand is a phosphine, such as triphenylphosphine; a monophosphite, such as tri methylolpropanephosphite or tris(2,4-di-tert-butylphenyl)phosphite; a bisphosphite; or a mixture of any of these.

The reactor effluent will typically comprise further components in addition to the product aldehyde and ligand-rhodium catalyst. Such further components may include olefins and paraffins, ligand decomposition products, ligand stabilisers, aldehyde oligomers (sometime referred to as 'heavies'), water and dissolved gases. The vapour mixture leaving the vaporiser will typically comprise further components in addition to the product aldehyde and strip gas. Such further components may include olefins, paraffins and other light components. The olefins and paraffins will typically condense in the condenser, while the light components will remain in the recycle strip gas, with their levels controlled by the purging of the purged strip gas stream.

The product aldehyde stream is preferably a liquid product aldehyde stream.

The reaction zone will be understood as describing one or more hydroformylation reactors. Typically, the reaction zone will comprise one, two, three, or four reactors. The reactors may, for example, be connected in series. Feed streams, such as the fresh syngas stream and the re-formed syngas stream, may be provided to one or more of the reactors and the reactor effluent that is passed to the vaporiser may be collected from one or more of the reactors.

Where it is said that a component, such as the product aldehyde, is vaporised, such as into the strip gas, it will be understood that a major portion of the component is so vaporised. A minor portion of the component may remain in the liquid phase, for example in equilibrium with the vaporised component in the vapour phase. It may be that at least 50 mol %, preferably at least 60 mol % and more preferably at least 70 mol % of the component is so vaporised. It may be that essentially all of the component is so vaporised. Similarly, where it is said that a component, such as the product aldehyde, is separated, such as from the vapour mixture, it will be understood that a major portion of the component is so separated. A minor portion of the component may remain. It may be that at least 75 mol %, preferably at least 90 mol % and more preferably at least 95 mol % of the component is so separated. It may be that essentially all of the component is so separated.

DESCRIPTION OF THE DRAWINGS

Embodiments of the present invention will now be described, by way of example, and not in any limitative sense, with reference to the accompanying drawings, of which.

DETAILED DESCRIPTION

Figure 1:
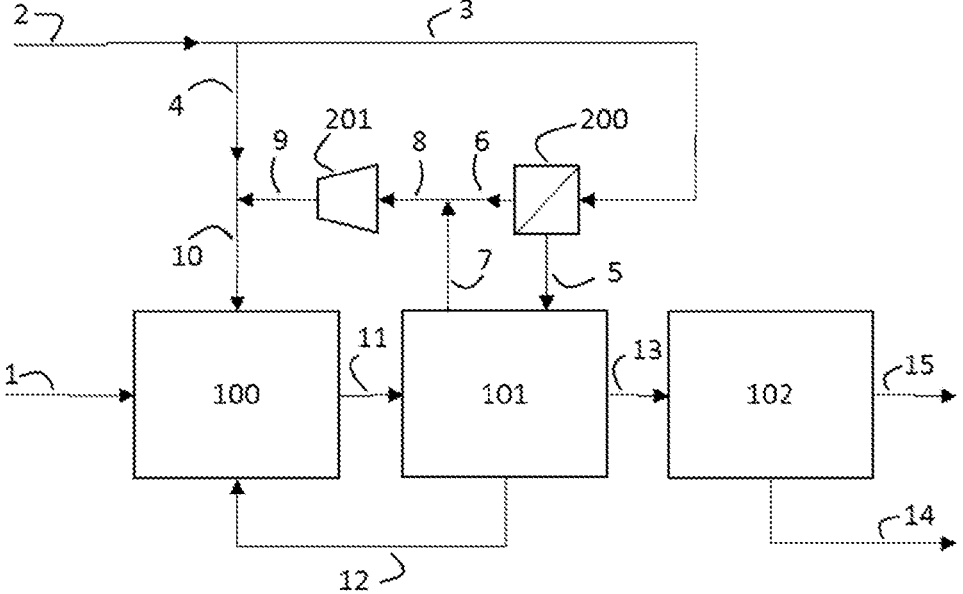
FIG. 1 is a block diagram of a flowsheet embodying the invention.

In FIG. 1 an olefin feed 1 is fed to a hydroformylation reaction zone 100. The reaction zone 100 comprises at least one reactor, and possibly two or three reactors, from which a reactor effluent 11 is passed to a catalyst separation unit 101. Liquid ligand-rhodium catalyst solution 12, with the solvent typically comprising heavies such as dimers or trimers, is recycled from the catalyst separation unit 101 to the reaction zone 100. Product aldehyde stream 13 is recovered from the catalyst separation unit 101 and passed to an aldehyde purification unit 102, from which purified aldehyde 15 is recovered. Olefins and paraffins 14 are also recovered from the aldehyde purification unit 102.

Syngas feed 2 is split into fresh syngas stream 4, which is fed directly to the reaction zone 100 as part of mixed syngas feed stream 10, and syngas stream 3, which is fed to membrane separation unit 200. In membrane separation unit 200, the syngas stream 3 is separated into make-up strip gas stream 5, which is passed to the catalyst separation unit 101, and hydrogen-containing stream 6, which is combined with purged strip gas stream 7 to form re-formed syngas stream 8, which is compressed in compressor 201 and fed 9 to the reaction zone 100 as part of mixed syngas feed stream 10. A purge may be included, for example from one or more of streams 6, 7, 8 or 9, for operational reason, but is preferably avoided so as to avoid loss of reformed syngas.

Figure 2:
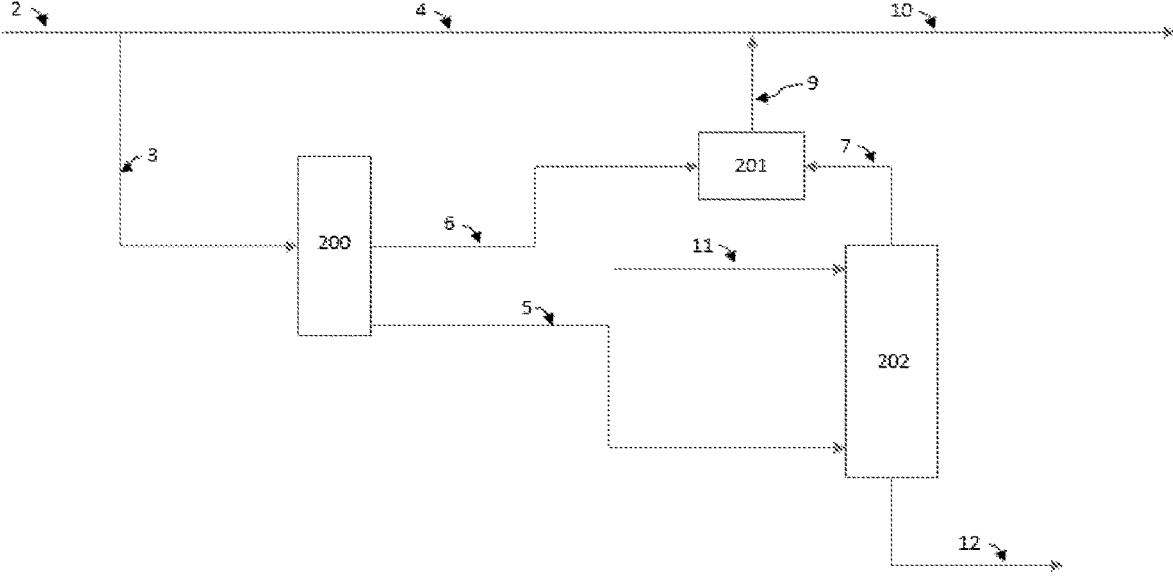
FIG. 2 is a process flow diagram of part of the process of FIG. 1 embodying the invention.

More detail of catalyst separation unit 101 is shown in FIG. 2. In FIG. 2, syngas feed 2 is split into fresh syngas stream 4 which is fed directly to the reaction zone 100 as part of mixed syngas feed stream 10, and syngas stream 3, which is fed to membrane separation unit 200. In membrane separation unit 200, the syngas stream 3 is separated into strip gas stream 5, which is passed to stripper 202, and hydrogen-containing stream 6, which is combined and compressed 201 with purged strip gas stream 7 to form re-formed syngas stream 9, which is fed to the reaction zone 100 as part of mixed syngas feed stream 10. Reactor effluent 11 is fed to stripper 202, which operates to produce a stripped effluent stream 12 having a lower hydrogen concentration than effluent stream 11, and which is passed to a catalyst separation unit.

Example 1

The following examples have been generated using a commercially available simulation package SimSci ProII v10.1. The use of simulations to evaluate new processes is well-established in the chemical engineering art.

Reactor effluent at 90° C. containing 0.8 mol % dissolved hydrogen is fed to a stripping column operating at 13.5 barg at the top of the column.

3.6 mol % of the plant syngas feed at 25 barg is fed to a membrane separation unit, where a CO-rich stream is generated. The CO-rich stream contains 96.4 mol % CO and 0.8 mol % hydrogen. The CO-rich stream with a flow of 1.36 $Nm^3$/tonne of aldehyde reactor product is fed to the bottom of the stripping column, which contains seven theoretical stages. It is contacted with the reactor effluent inside the column and a stripped effluent stream containing 0.08 mol % hydrogen in predominantly $C_8$ and $C_9$ oxygenates is produced at the bottom of the stripping column.

The stripped effluent stream leaving the stripping column is then fed to the catalyst separation unit operating at 12 barg, where the product oxygenates are contacted with 3,240 $Nm^3$/tonne of aldehyde reactor product of cycle gas at 140° C. to vaporise most of the reactor product leaving the catalyst solution to be recycled back to the reactors. The concentration of hydrogen in the cycle gas is 1.56 mol %.

The purged strip gas stream leaving the top of the stripping column is cooled to 45° C. to remove condensable hydrocarbons and return them to the stripper column. The cooled purged strip gas is then combined with the hydrogen-rich gas from the membrane separation unit, recompressed to 25 barg to be returned to the reactors.

For the purposes of comparison and to illustrate the benefits of the invention, an arrangement from prior art was also simulated using the same commercially available simulation package SimSci ProII v10.1.

Reactor effluent of the same composition as described above, also at 90° C. and also containing 0.8 mol % dissolved hydrogen is fed directly to the catalyst separation unit operating at 12 barg, where the product oxygenates are contacted with 3,240 $Nm^3$/tonne of aldehyde reactor product of cycle gas at 140° C. to vaporise most of the reactor product leaving the catalyst solution to be recycled back to the reactors.

A CO-rich make-up stream is generated by sending all of the plant feed syngas to a membrane separation unit. The CO-rich make-up stream of 37.14 Nm³/tonne of aldehyde reactor product is produced and added to the cycle gas. A purge of 38.79 Nm³/tonne of aldehyde reactor product is removed from the cycle gas to purge hydrogen and inert components. The cycle gas contains 1.94 mol % of hydrogen.

The example demonstrates that the process of the present invention achieves a low hydrogen concentration in cycle gas using a much lower flow of CO-rich gas than required in the arrangement disclosed in prior art, thereby reducing energy consumption and equipment size.

Example 2

General procedure: All tests were conducted in a multi-well heating block fitted with six 100 mL autoclaves, with several tests run in duplicate for increased accuracy. The temperature was controlled using an internal thermocouple and double checked against one autoclave with an internal thermocouple to measure the process temperature as a cross check. Phosphorous ligand (in a molar excess) and rhodium stock solution (prepared by dissolving Rh(acac) (CO)₂ in toluene; 50 mL of solution charged) were transferred into a 100 ml autoclave before sealing and purging with syn gas (CO:H₂ molar ratio=1:1; 3×100 psi(g)). All autoclaves were then pressurised with syn gas and left to form the active catalyst in situ, then left to cool to ambient temperature. Once cool, a sample (1.5 ml) from the autoclave was taken for rhodium analysis via ICP-OES analysis. The autoclave was then purged with the appropriate test gas (syn gas, CO, H₂ or N₂), and then pressurised to the test pressure with the test gas (as outlined in Table 1, below). The reactions were then run for their allotted time period, before removing the autoclaves from the heating block and allowing to cool to room temperature. On the completion of the test, a further sample was removed from the autoclave to analyse for rhodium concentration via ICP-OES to look for soluble rhodium loss during the course of the experiment. The percentage loss of rhodium was then calculated=((1−[Rh]$_{Final}$/[Rh]$_{Initial}$)×100.

The loss of rhodium with time have been inputted into Table 1, below, showing dependency on the different gas compositions are varying pressures. Entries 1 and 2 show high losses of rhodium under a syn gas atmosphere at 120° C., with a minor improvement at the higher pressure (~90%). Under nitrogen at identical conditions (Entry 3) shows a significant improvement to the rhodium loss with only 5% loss of rhodium. In a CO only atmosphere (Entry 4), no rhodium loss was evident. This clearly shows the benefit of operating in the absence of hydrogen, but also the increased stabilising effect of CO versus nitrogen.

When operating at higher temperatures (130° C., Entries 5-8), higher pressures were investigated in an attempt to increase stability of the rhodium catalyst. Using a 1:1 syn gas composition (Entry 5), losses were 93%. Operation at higher pressures with high H₂:CO ratios (entry 6) reduced the losses to 69%. Complete loss of rhodium was observed in a hydrogen only atmosphere (Entry 7). However, even under these forcing conditions, the rhodium loss under a pure CO atmosphere was only 12% (Entry 8). Although losses were reduced when using a high H₂:CO atmosphere (Entry 6), it is assumed that the high partial pressure of CO has a stabilising effect on the catalyst solution. However, the results from both sets of experiment show a clear benefit to loss of rhodium from the catalyst solution when using a CO only atmosphere.

TABLE 1

| Entry | Rx Time (hours) | Temperature (° C.) | CO pp (psi(g)) | H₂ pp (psi(g)) | N₂ pp (psi(g)) | % Rh loss |
|---|---|---|---|---|---|---|
| 1 | 64 | 120 | 2 | 2 | | 92.78 |
| 2 | 64 | 120 | 4 | 4 | | 89.53 |
| 3 | 64 | 120 | | | 8 | 5.38 |
| 4 | 64 | 120 | 8 | | | 0.00 |
| 5 | 120 | 130 | 50 | 50 | | 91.76 |
| 6 | 120 | 130 | 112 | 224 | | 68.86 |
| 7 | 120 | 130 | | | 100 | 99.16 |
| 8 | 120 | 130 | 100 | | | 12.22 |

It will be appreciated by persons skilled in the art that the above embodiments have been described by way of example only, and not in any limitative sense, and that various alterations and modifications are possible without departure from the scope of the invention as defined by the appended claims.

The invention claimed is:

1. A process for producing an aldehyde, the process comprising:
   hydroformylating an olefin in a hydroformylation section to form the aldehyde using a hydroformylation catalyst;
   recovering an effluent stream comprising the aldehyde, hydrogen and the hydroformylation catalyst;
   passing the effluent stream to a stripper;
   feeding a syngas stream to a separation system;
   separating the syngas stream into a hydrogen rich stream and a carbon monoxide rich stream in the separation system; and using the carbon monoxide rich stream as a strip gas;
   contacting the effluent stream with the strip gas comprising the carbon monoxide rich stream in the stripper to produce a stripped effluent stream having a lower hydrogen concentration than the effluent stream; and
   recovering the stripped effluent stream.

2. A process according to claim 1, wherein the separation system comprises a membrane or a cryogenic distillation unit.

3. A process according to claim 1, wherein the process comprises: recovering a used strip gas stream, comprising the strip gas and hydrogen, from the stripper; combining the used strip gas stream with the hydrogen rich stream to form a recombined syngas stream; and feeding the recombined syngas stream to the hydroformylation section.

4. A process according to claim 3, wherein the process comprises splitting the syngas stream fed to the separation system from a syngas feed stream to the hydroformylation section.

5. A process according to claim 4, wherein the recombined syngas stream is fed to the hydroformylation section by mixing the recombined syngas stream with the syngas feed stream.

6. A process according to claim 1 wherein the hydroformylation catalyst comprises a homogenous metal-ligand catalyst.

7. A process according to claim 6, wherein the homogeneous metal-ligand catalyst comprises rhodium.

8. A process according to claim 6, wherein the metal-ligand catalyst comprises an organophosphite or organophosphine ligand.

9. A process according to claim 8, wherein the organophosphite or organophosphine ligand comprises triphenylphosphine.

10. A process according to claim 1, wherein the process comprises feeding the stripped effluent stream to a vaporiser and recovering from the vaporiser a vapour stream comprising: (1) the aldehyde, and (2) a liquid catalyst recycle stream comprising the hydroformylation catalyst for recycle to the hydroformylation section.

11. A process according to claim 10, wherein the molar composition of hydrogen in the stripped effluent stream is not more than 5 mol %.

12. A process according to claim 10, wherein the process comprises feeding a gas comprising carbon monoxide to the vaporiser.

* * * * *